(12) United States Patent
Ries et al.

(10) Patent No.: US 9,381,086 B2
(45) Date of Patent: Jul. 5, 2016

(54) STEM FOR USE IN JOINT ARTHROPLASTY

(75) Inventors: Michael D. Ries, Tiburon, CA (US); Desmond O'Farrell, Grand Rapids, MI (US); Andrew John Rodenhouse, Grand Rapids, MI (US); Stephen B. Gunther, Cloverdale, CA (US)

(73) Assignee: Shoulder Innovations, LLC, Ann Arbor, MI (US)

( * ) Notice: Subject to any disclaimer, the term of this patent is extended or adjusted under 35 U.S.C. 154(b) by 116 days.

(21) Appl. No.: 13/308,221

(22) Filed: Nov. 30, 2011

(65) Prior Publication Data

US 2012/0172996 A1 Jul. 5, 2012

Related U.S. Application Data

(60) Provisional application No. 61/418,346, filed on Nov. 30, 2010.

(51) Int. Cl.
| | | |
|---|---|---|
| A61F 2/36 | (2006.01) | |
| A61F 2/40 | (2006.01) | |
| A61F 2/30 | (2006.01) | |

(52) U.S. Cl.
CPC .............. *A61F 2/3662* (2013.01); *A61F 2/36* (2013.01); *A61F 2/4059* (2013.01); *A61F 2002/3013* (2013.01); *A61F 2002/30158* (2013.01); *A61F 2002/30176* (2013.01); *A61F 2002/30772* (2013.01); *A61F 2002/30884* (2013.01); *A61F 2002/30892* (2013.01); *A61F 2002/368* (2013.01); *A61F 2002/3668* (2013.01)

(58) Field of Classification Search
CPC .............................. A61F 2/3662; A61F 2/4059
USPC .......... 623/19.11–19.14, 23.15, 23.18–23.35, 623/23.44
See application file for complete search history.

(56) References Cited

U.S. PATENT DOCUMENTS

| | | | | |
|---|---|---|---|---|
| 2,781,758 | A | * | 2/1957 | Chevalier ................... 623/23.28 |
| 4,404,693 | A | * | 9/1983 | Zweymuller ............... 623/23.29 |
| 5,314,489 | A | | 5/1994 | Hoffman et al. |
| 5,514,184 | A | | 5/1996 | Doi |
| 5,755,811 | A | * | 5/1998 | Tanamal et al. ............ 623/23.35 |
| 7,044,973 | B2 | | 5/2006 | Rockwood et al. |
| 7,517,364 | B2 | | 4/2009 | Long et al. |
| 7,749,278 | B2 | | 7/2010 | Frederick et al. |
| 7,776,098 | B2 | | 8/2010 | Murphy |
| 8,007,538 | B2 | | 8/2011 | Gunther |
| 8,048,167 | B2 | | 11/2011 | Dietz et al. |
| 2003/0100952 | A1 | | 5/2003 | Rockwood, Jr. et al. |
| 2004/0107002 | A1 | | 6/2004 | Katsuya |
| 2004/0193277 | A1 | | 9/2004 | Long et al. |
| 2007/0050042 | A1 | | 3/2007 | Dietz et al. |
| 2007/0112433 | A1 | | 5/2007 | Frederick et al. |
| 2010/0087876 | A1 | | 4/2010 | Gunther |

(Continued)

OTHER PUBLICATIONS

Mar. 9, 2012, International Search Report and Written Opinion for International Application No. PCT/US2011/062702.
Braun, et al., Modular Short-stem Prosthesis in Total Hip Arthroplasty: Implant Positioning and the Influence of Navigation, ORTHO SuperSite (Oct. 2007).

(Continued)

*Primary Examiner* — Thomas J Sweet
*Assistant Examiner* — Megan Wolf
(74) *Attorney, Agent, or Firm* — Knobbe, Martens, Olson & Bear, LLP

(57) ABSTRACT

The invention relates to a prosthesis for implantation into a long bone during joint arthroplasty, particularly Total Shoulder Arthoplasty and Total Hip Arthroplasty, and a method for use of the implant.

28 Claims, 19 Drawing Sheets

(56) References Cited

U.S. PATENT DOCUMENTS

2010/0087877 A1 4/2010 Gunther
2010/0249938 A1 9/2010 Gunther et al.
2011/0313533 A1 12/2011 Gunther
2013/0060346 A1 3/2013 Collins

OTHER PUBLICATIONS

Panisello, et al., Bone remodelling after total hip arthroplasty using an uncemented anatomic femoral stem: a three-year prospective study using bone densitometry, J Ortho Surg 14(1):32-37 (2006).

* cited by examiner

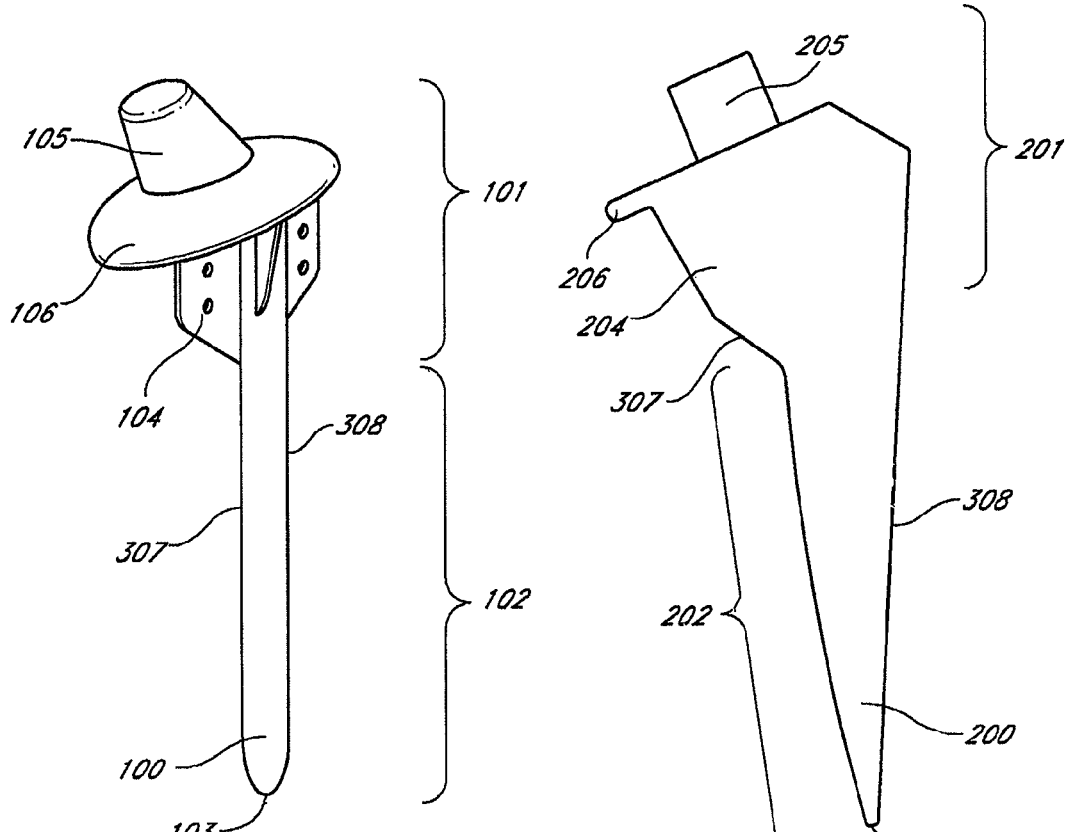
FIG. 1
PRIOR ART
FIG. 2
PRIOR ART
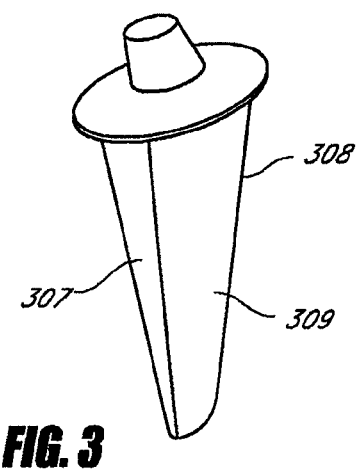
FIG. 3
PRIOR ART
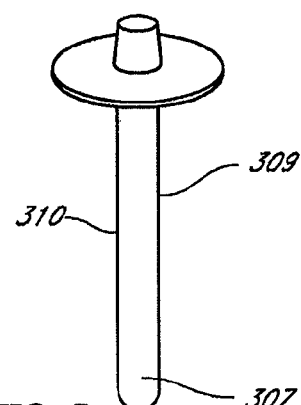
FIG. 4
PRIOR ART

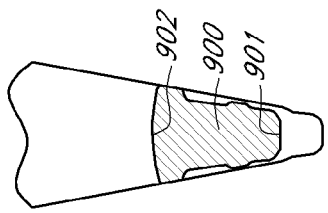
FIG. 10D
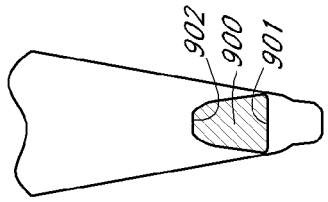
FIG. 10I
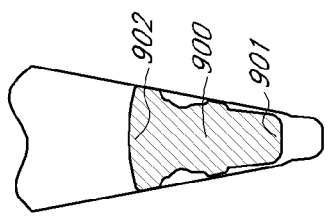
FIG. 10C
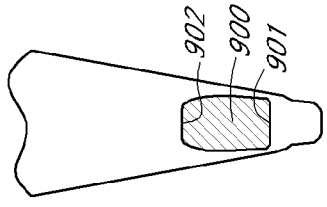
FIG. 10H
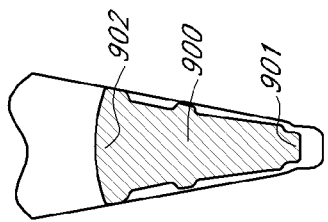
FIG. 10B
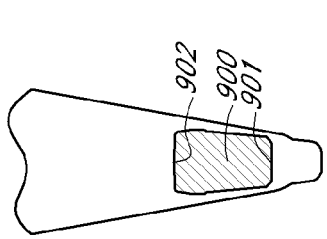
FIG. 10G
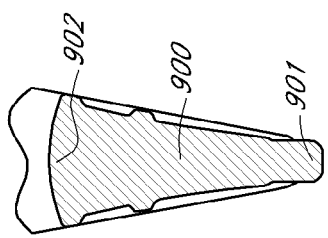
FIG. 10A
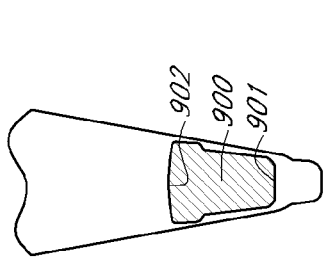
FIG. 10F
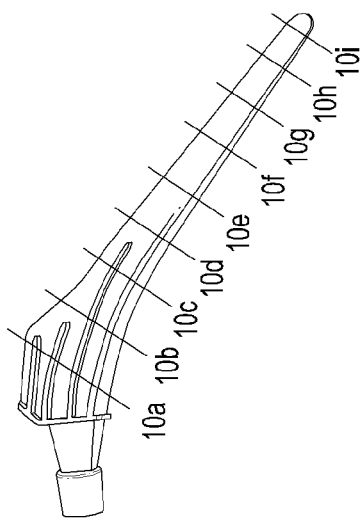
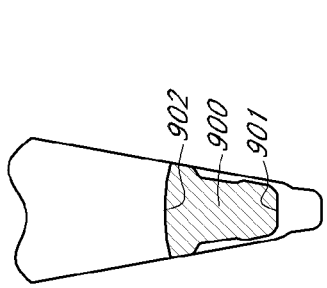
FIG. 10E

STEM FOR USE IN JOINT ARTHROPLASTY

PRIORITY CLAIM

This application claims priority under 35 U.S.C. §119(e) to U.S. Provisional Application No. 61/418,346, filed on Nov. 30, 2010; the entirety of which is incorporated by reference herein and made a part of the present specification.

BACKGROUND OF THE INVENTION

1. Field of the Invention

The invention relates to, in some aspects, the geometry of a stem for implantation within long bones during joint arthroplasty, particularly as it relates to Total Hip Arthroplasty or Total Shoulder Arthroplasty.

2. Description of the Related Art

Total joint arthroplasty is an established surgical treatment of diseased joints and is effective in the relief of pain and the restoration of function of disease compromised joints. Successful joint arthroplasty results in the restoration of functionality, mobility, and quality of life to patients who would otherwise be disabled as a result of joint disease.

A typical surgical procedure involves the surgical exposure of the affected joint, resection and excision of diseased bone tissue and the replacement of the excised tissue with a manufactured, mechanical joint set. The joint components may be attached to native bone by means of conventional fasteners, bone cements or interference fitting of the components within prepared cavities in the native bone structure.

A typical joint set comprises a rigid stem placed within the medullary canal of the long bone of the joint, typically manufactured from stainless steel, titanium, chromium cobalt alloy or other bio-compatible metal, a generally spherical or convex articulating component, typically manufactured of a metallic alloy or ceramic material and a corresponding concave articulating surface, typically manufactured from a polymer or ceramic material.

Exposure of the joint structure may be accomplished by a surgical approach which is directed posteriorly or by an approach which is directed anteriorly to the femur or humerus. In hip surgery the posterior approach is currently used by many surgeons as it allows for a wide exposure of the bone structures and good visualization within the wound. In shoulder surgery an anterior approach is typical. In many instances the surgical approach is dictated by the size and geometry of the implant devices being used. The current approaches typically result in a large incision size with associated muscle dissection and may be disruptive to patient anatomy. Recently, various minimally invasive techniques have been developed which require smaller incision sizes. An anterior approach to the hip joint structure has been developed and attempts are being made to minimize the incision and exposure of the shoulder joint. Associated with these techniques is a reduced exposure of, and access to, the bones within the joint structure. In addition, the reduced exposure and access pose substantial challenges to the surgeon as they relate to resecting diseases of the bone, preparing the native bone to receive implant devices, and inserting many of the implant devices currently available. The degree of difficulty associated is often higher, can result in higher complication rates when compared to conventional procedures with larger surgical exposures, and may require extended surgery times. Further, surgical outcomes are varied, depending upon surgeon skill and the nature of the defects in the native bone. As a consequence there is a need for implant components, particularly long bone implant components, which are compatible with smaller incisions and more restricted access to the native bone.

A further consequence of the small exposure is the limited space available to the surgeon within the joint wherein interoperative adjustment of implant position can be made.

The axial position of the stem within the femoral or humeral bone is of particular importance. Misalignment of the stem with respect to the natural axis of the bone (known as varus and valgus mal-alignment) can result in abnormal biomechanics of the joint and atypical stress distributions within the bone structure which may result in implant loosening, dislocation, pain, or may cause fractures of the bone. Mal-alignments may result from poor surgical technique, inadequate exposure of the femur, incompatibility of instruments and implants with the surgical approach, or from natural deformities of the native bone within the medullary canal or metaphyseal regions of the bone.

Mal-alignment of the implanted stem may result in aseptic loosening of the implant or localized remodeling of the native cortical bone over time, ultimately causing failure of the implant and requiring additional revision surgeries to be performed to repair or replace the implant. These problems are well described and discussed in the published literature, including but not limited to, Panisello et al., (Journal of Orthopedic Surgery; 2006 April; 14(1): 32-37), Braun et al. (OrthoSupersite; October 2007), Ozturk et al. (Jun. 3, 2010), U.S. Patent Pub. No. 2004/0107002 to Katsuya, U.S. Patent Pub. No. 2008/0091274 to Murphy, U.S. Pat. No. 5,314,489 to Hoffman et al., and U.S. Pat. No. 5,514,184 to Doi et al., the descriptions of the clinical issues associated with stem alignment, biomechanics and implant failure being incorporated herein by reference in their entireties.

The aforementioned patents, publications, and articles incorporated by reference contain therein various designs and methods directed at addressing the previously discussed issues.

Various embodiments of implant stems have been described in the prior art in an attempt to resolve the issues previously described. Certain conventional stems have a proximal portion designed to locate within the metaphysis of the femur or of the humerus and a distal portion disposed to be located within the medullary canal of the bone. The proximal portions of these stems are either generally cylindrical or rectilinear (rectangular, triangular or trapezoidal) in shape when viewed in cross section along the proximal to distal axis of the implant and are intended to generally fill the metaphyseal region of the bone, the distal portion of each embodiment being narrow forms and being elongated so as to fit within the intramedullary canal of the distal region bone.

In general, the design of currently available implant stems involves the axial cross sections of the implant along the axis from the proximal portion to the distal end wherein the cross sectional profile is constant but the cross sectional area of the implant taken in a plane substantially perpendicular to the longitudinal axis reduces from the proximal to distal end.

Further, the cross sections are generally wider at the medial side than at the lateral side all along the axis of the implant. The distal portions of some implants may be cylindrical and may incorporate a variety of features including protrusions or secondary components in order to center the distal portion within the medullary canal and aid with implant alignment and fixation.

Disclosed herein is a novel design for a stem to be used within long bones during joint repair surgery.

SUMMARY OF THE INVENTION

There is provided in accordance with some embodiments a long bone implant for use in joint arthroplasty comprising a first end, a second end comprising a blunt tip, and a stem of the implant disposed between the first and second ends, such that a proximal portion of the stem comprises an anterior surface, a posterior surface, a medial surface and a lateral surface, wherein a measure of said medial surface taken in a plane perpendicular to the longitudinal axis of the implant is greater than a measure of said lateral surface taken in the same plane and a distal portion of the stem comprises an anterior surface, a posterior surface, a medial surface, and a lateral surface wherein a measure of said lateral surface taken in a plane perpendicular to the longitudinal axis of the implant is greater than a measure of the medial surface taken in the same plane.

In some embodiments, in the proximal portion of the stem, the medial surface dimension or measure (e.g., a transverse dimension) taken in a first plane perpendicular to the longitudinal axis of the implant comprises a dimension or measure 5% to 100%, or more, greater than the lateral surface measure in the same plane and, in the distal portion of the stem, the lateral surface taken in a second plane perpendicular to the longitudinal axis of the implant comprises a dimension or measure 5% to 100%, or more, greater than the medial surface dimension measure taken in the same plane. This results in large load bearing areas on the wide medial surface proximally and on the wide lateral surface distally. This also promotes self-centering of the implant in the medullary canal, avoiding varus or valgus mal-alignment.

In one embodiment of the invention, the implant is a femoral implant for use in hip arthroplasty. In some embodiments, the implant has one, two, three, four, or more axially oriented protrusions on the anterior surface, posterior surface, or both, which act, during implantation, as guide rails. In some embodiments, there are relatively medial and lateral guide rails on the anterior and posterior surfaces. In some embodiments of the invention, the medial guide rail extends further distally than the lateral guide rail, the lateral guide rail extends further distally than the medial guide rail, or they can extend the substantially same distance. The guide rails can serve multiple purposes. They help guide the implant during insertion, prevent rotation of the implant during and after insertion, and provide spaces between the rails for compacted cancellous bone, which increases the stability of the inserted implant. In another embodiment of the femoral implant, there are one, two, three or more voids on the proximal portion of the implant on the anterior surface, posterior surface, or both. These voids may be round, or any appropriate shape. The voids accommodate compressed cancellous bone during insertion or accommodate bone cement dispensed to assist fixation of the implant. In other embodiments, there are no voids.

In a further embodiment of the femoral implant, there is a lateral keel. Where the lateral keel arises on the proximal portion of the implant, there is a localized reduction in the cross section of the implant, when compared to adjacent sections of the keel laterally and stem medially. This allows minimized displacement of cancellous bone during insertion, reducing forces during insertion and also resists rotation of the implant both during and after insertion. In other embodiments, there is no lateral keel, or a keel without localized reduced cross section of the implant. In some embodiments, the length of the femoral implant is 100 to 130 mm. In other embodiments, it may be less than 100 mm or more than 130 mm.

In a further embodiment, the implant is a humeral implant for use in shoulder arthroplasty. In some embodiments, the implant has one, two, three, four or more stabilization ribs which provide mechanical structure, resist rotation of the implant within the bone, and enhance stability of the implant within the bone after implantation. In some embodiments, the ribs are on the anterior surface, posterior surface, or anterior and posterior surfaces. In other embodiments, there is a stabilization fin on the lateral aspect of the proximal surface. In some embodiments of the invention, the implant includes a collar proximally to rest on the cortical bone and prevent subsidence of the implant into the humerus after implantation. In other embodiments, there is no collar. In some embodiments the implant has an overall length of 70 to 90 mm. In other embodiments, the implant has a length less than 70 mm, preferably about 60 mm. In some embodiments of the invention, the medial and lateral surfaces of the implant are curved, e.g., arcuate longitudinally. In other embodiments, the medial surface is arcuate, while the lateral surface is straight, or having an axis that is parallel or substantially parallel to a central longitudinal axis of the implant. In still other embodiments, neither the medial nor lateral surface is curved, e.g., arcuate along the length of the implant.

In accordance with a further aspect, there is provided an implant comprising a first end, a second end comprising a distal tip, e.g., a blunt distal tip, and disposed between the first and second ends, a stem comprising an anterior surface, a posterior surface, a medial surface, and a lateral surface, wherein either or both of a measure or dimension of the medial surface and a measure of the lateral surface taken in a plane substantially perpendicular to the longitudinal axis of the implant change from proximal to distal, such that a ratio of the medial measure to the lateral measure changes from proximal to distal along the longitudinal axis of the implant.

In some embodiments, the width of the medial surface and width of the lateral surface change continuously along the length of the stem. In other embodiments, the change is not continuous.

In some embodiments, the measure of the medial surface taken in a plane substantially perpendicular to the longitudinal axis of the implant generally decreases from proximal to distal along the stem and the measure of the lateral surface taken in a plane substantially perpendicular to the longitudinal axis of the implant generally increases from proximal to distal along the stem.

In some embodiments, the entire stem portion, or a portion thereof, is coated with a porous material for aiding in the fixation of the stem in the long bone for a press fit implant. In other embodiments, the implant is designed for cement fixation and can have a smooth surface or a roughened, textured surface.

In accordance with a further embodiment, there is provided a method for implanting a stem in a long bone during joint arthroplasty. The method comprises identifying a patient having identifying a patient having a diseased joint, surgically exposing the joint surface, excising an articulating portion of a long bone, preparing a proximal portion of the long bone to receive an implant, implanting a stem into the proximal portion and intramedullary canal of the long bone, said stem comprising a medial, a lateral, an anterior, and a posterior surface, the surfaces comprising a geometry such that the ratio of medial surface measure to lateral surface measure taken in a plane substantially perpendicular to the longitudinal axis of the stem changes along the stem from proximal to distal The method may additionally comprise the step of securing the implant using bone cement, such as polymethylmethacrylate (PMMA) or a compatible fixation material. Alternatively, the implant can be press-fit.

Another aspect of the invention features a minimal incision shoulder arthroplasty technique that allows replacement of the glenoid surface and humeral head with only a small incision and less extensive soft tissue stripping. The "mini-incision" procedure also leaves the pectoralis tendon and the majority of the inferior capsule intact. The advantages of the "mini-incision" procedure include a shorter incision with less scarring, increased safety, and a more simple exposure of the glenoid, thus allowing general orthopedists to perform a shoulder replacement with less difficulty and potentially fewer complications. The skin incision is preferably less than 10 cm. in length, more preferably between 7 and 10 cm.

Further features and advantages will become apparent to those of skill in the art in view of the detailed description of embodiments which follows, when considered together with the attached drawings and claims.

BRIEF DESCRIPTION OF THE DRAWINGS

FIG. 1 is an anterior surface view of an implant device for implantation in the humerus.

FIG. 2 is an anterior surface view of an implant device for implantation in the femur.

FIG. 3 is an anteromedial surface view of a long bone implant.

FIG. 4 is a medial surface view of a long bone implant.

FIG. 10A-10I are schematic cross sectional areas (not necessarily to scale) of a femoral implant at approximately 10 mm intervals from a first end of the implant to a second end of the implant.

DETAILED DESCRIPTION

Figure 5:
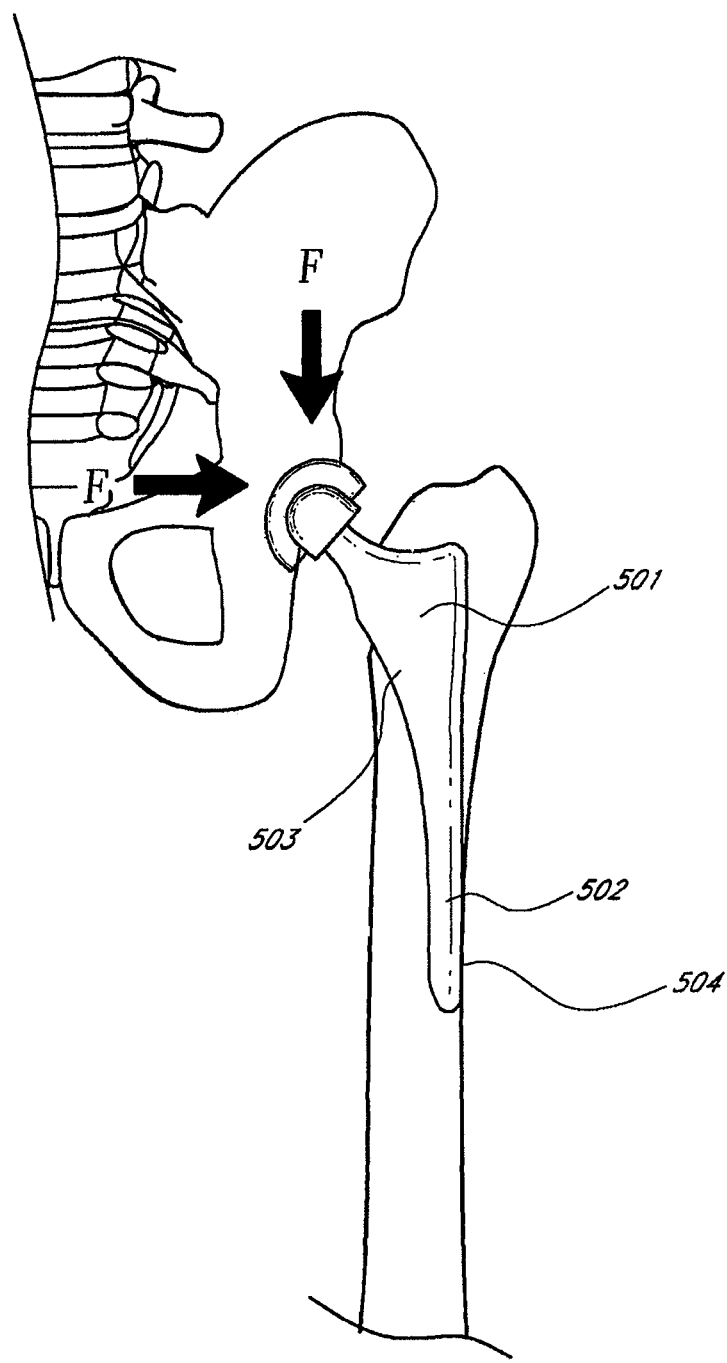
FIG. 5 is a view of a femoral implant with varus mal-alignment.

Referring now to FIGS. 1 and 2, these figures illustrate current implant devices for implantation in humeral and femoral bones respectively. Implants used in the humerus (100) during joint arthroplasty have a proximal region (101) and a stem portion (102), the distal portion terminating in a distal tip (103). The proximal portion of the humeral implant may have flanges (104) protruding radially from the proximal stem region, these flanges being disposed in a manner to resist rotation of the implant within the cancellous bone after implantation within the humerus. The proximal portion will further have a receiving feature (105) for the purpose of mechanically coupling to an articulating component of the joint replacement system. Humeral stem implants will typically have a flange feature (106) intended to restrict the penetration of the implant within the native bone and to resist post-operative subsidence of the implant under anatomical loading conditions. Humeral stem implants are typically 120 mm to 160 mm in length and femoral stems are typically in the range of 150 mm to 200 mm in length.

Implants used in the femur during joint arthroplasty are of a similar construct to those used in humeral joint arthroplasty. Referring to FIG. 2 the implant (200) has a distal region (202), a blunt distal tip (203), a proximal region (201), and a coupling means (205) to receive an articulating surface component. The proximal region (201) may have various features or surface treatments (204) thereon for the purpose of improving torsional stability of the implant within the bone after implantation. The implant may or may not also have a medial collar (206) proximally to rest on cortical bone and prevent subsidence of the implant.

Referring now to FIGS. 3 and 4, all long bone implants can be generally described as having a medial surface (307), a lateral surface (308) an anterior surface (309) and a posterior surface (310), these surfaces corresponding to the orientation of the implant within the bone after implantation.

In the implants currently available or disclosed within prior art the proportionate relationship between the medial surface and the lateral surface is generally constant; at any distance along the stem, the medial surface being greater than that of the lateral surface, or vice-versa.

The surgical technique associated with these stems in both humeral and femoral applications is generally similar, irrespective of the implant design; the joint structure is surgically exposed through an incision that is generally 120 mm to 200 mm in length, the spherical component of the long bone is resected and removed from the joint, a cavity is prepared within the long bone to receive the stem implant by removing native cancellous bone from within the bone by drilling and broaching, and the stem implant is fitted within the long bone. The distal portion of the implant extends through and within the intramedullary canal of the bone; the proximal portion is embedded within cancellous tissue at the proximal aspect of the bone. The implant may be secured by press fitting within the native bone, by the application of bone cements, or by other secondary fastening means.

The final position and orientation of the implant device is at best variable, being subject to influences of the surgeon's skill, the access to the bony structures available through the surgical incision, the trajectory established by the drilling and broaching steps in the procedure, native anomalies of the bone structure, and the patient's general anatomy.

As a consequence of this variability, it is not unusual to have implants that are in sub-optimal or compromising positions. Mal-position of the implant may lead to adverse clinical outcomes, including loosening of the implant, post-operative mechanical instability of the joint, overstuffing of the joint, or peri-prosthetic fracture of the bone during or after surgery.

Referring now to FIG. 5, a femoral implant is shown located within the femur; the proximal portion of the implant (501) has a medial bias while the distal portion of the implant (502) has a lateral bias. This is known as varus mal-alignment. In this position the implant device transfers anatomic loads (F) through the implant and couples these loads to the native bone disproportionately at the proximal medial position (503) and the distal lateral position (504) and effectively induces a cantilever effect which concentrates forces at the distal region (504). These forces may cause peri-prosthetic fractures of the bone in the distal region of the implant (504).

Figure 6:
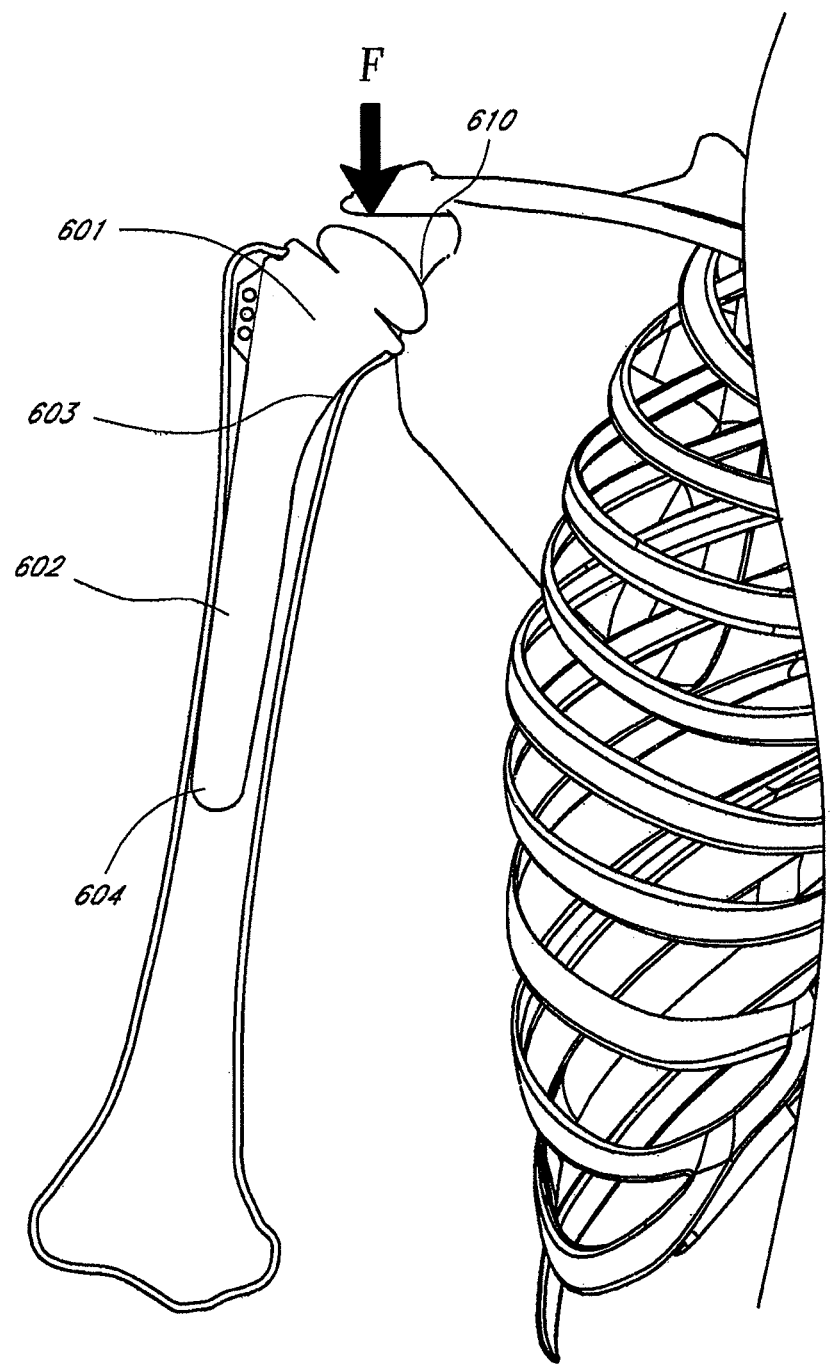
FIG. 6 is a view of a humeral implant placed in varus mal-alignment.

Similarly, now referring to FIG. 6, a humeral implant (601) has been mal-positioned in a similar varus manner, with which results in overstuffing of the joint (610) and an increased risk of peri-prosthetic fracture at the distal lateral region (604).

Figure 7:
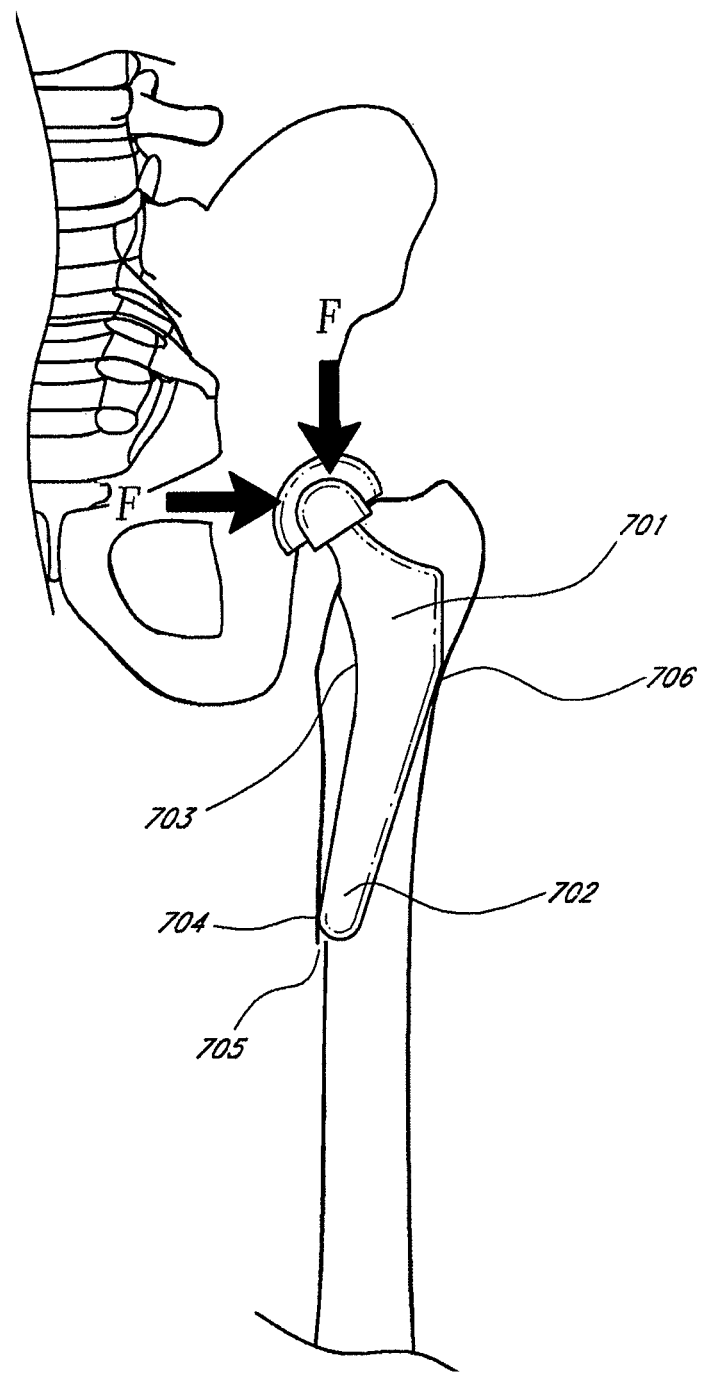
FIG. 7 is a view of a femoral implant placed in valgus mal-alignment with associated peri-prosthetic femur fracture.

Referring to FIG. 7, a femoral implant is shown located within the femur. The proximal portion of the implant (701) has a lateral bias and the distal portion of the implant (702) has a medial bias. This is known as valgus mal-alignment of the implant. Loads are disproportionately borne at the proximal lateral position (706) and distal medial position (704) of the bone. Further shown here is a peri-prosthetic fracture (705) of the femur which has resulted from forces (F) being inappropriately communicated to the medial aspect of the distal tip of the implant (704) and therefrom through the femur bone resulting in a fracture.

There remains a need for an implant device which can be implanted within long bone structures during joint arthroplasty which eliminates the variability of positioning, reduces the surgical variability, and is less invasive and less traumatic to the patient.

Figure 8:
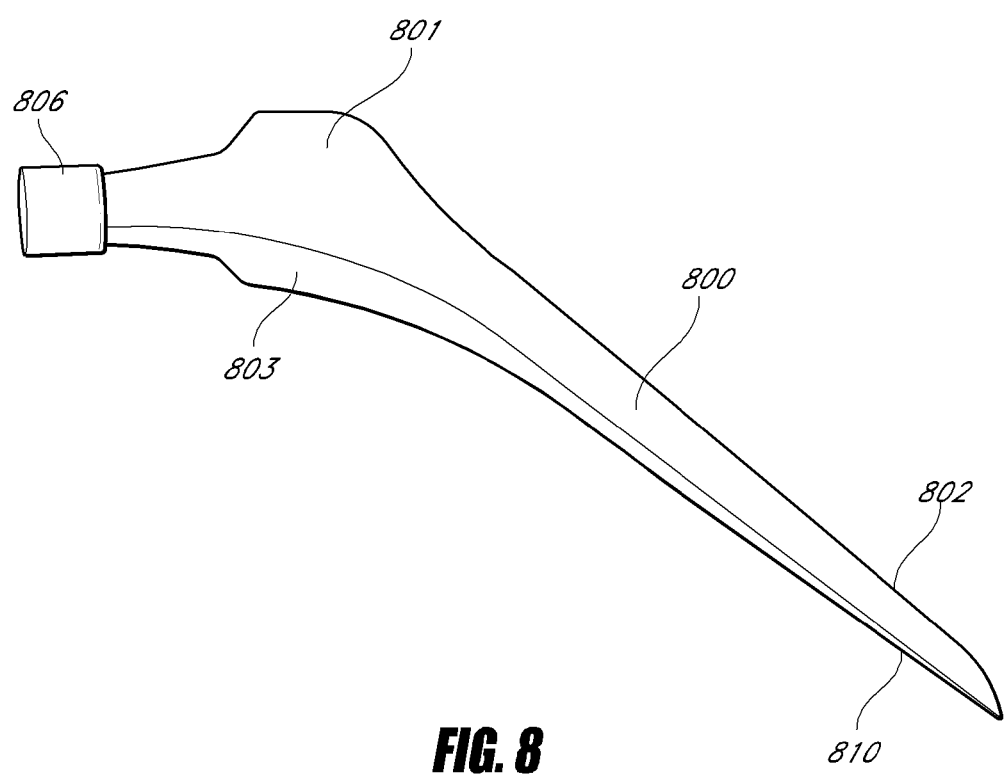
FIG. 8 is an anterior surface view of a femoral implant showing the varying width of the medial surface from proximal to distal along the stem.
Figure 9:
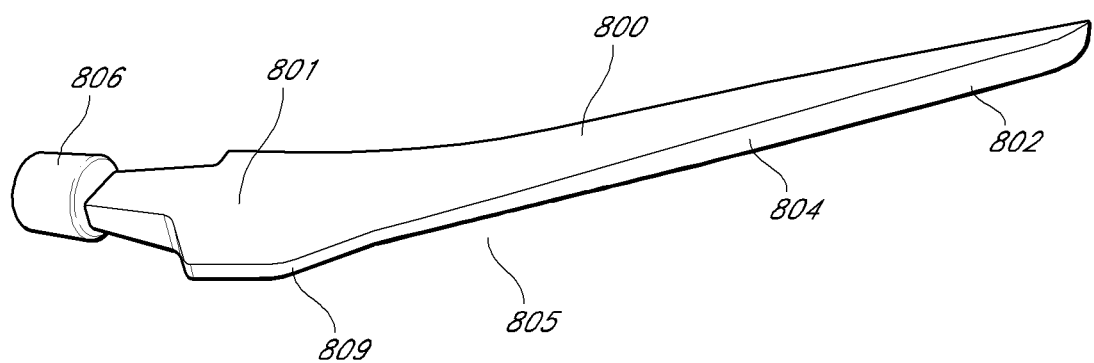
FIG. 9 is an anterior surface view of a femoral implant showing the varying width of the lateral surface from proximal to distal along the stem.

Referring then to FIGS. 8 and 9, there is disclosed one embodiment of a femoral implant stem (800) for use in hip joint arthroplasty, the implant having a proximal portion (809), a distal portion (802), a medial surface (803), a lateral surface (804), an anterior surface (801), a posterior surface (805) and a coupling feature (806) adjacent to the neck of the implant for receiving the articulating element of a joint arthroplasty system.

The implant stem (800) has a first, longitudinal axis. The first, e.g., medial surface (803) has an axial dimension, such as a width, larger than that of an axial dimension of the second, e.g., lateral surface in the proximal region of the stem along a second axis transverse to the longitudinal axis and which in some embodiments is generally continuously decreasing in dimension (e.g., width) from the proximal end (803) to the distal end (810) of the implant (in other words, along the longitudinal axis of the stem (800)) and a lateral surface (804) at the distal end which has an axial dimension (e.g., width) which is larger than that of an axial dimension of the medial surface in the distal region of the stem and which is generally increasing in dimension (e.g., width) from the proximal (809) to the distal end (809). In some embodiments, the axial dimension of the medial surface (803) in a plane transverse to the longitudinal axis of the stem in the proximal region of the stem is at least about 5%, 10%, 15%, 20%, 25%, 30%, 35%, 40%, 50%, 75%, 100%, or more greater than a corresponding axial dimension of the lateral surface in the proximal region of the stem along an axis transverse to the longitudinal axis of the stem in the proximal region of the stem in the same plane. The axial dimension of the lateral surface (804) in a plane transverse to the longitudinal axis of the stem the distal region of the stem can, in some cases, be at least about 5%, 10%, 15%, 20%, 25%, 30%, 35%, 40%, 50%, 75%, 100%, or more greater than the axial dimension of the medial surface in the distal region of the stem transverse to the longitudinal axis of the stem in the distal region of the stem in the same plane. In some embodiments, the axial dimension of the medial surface (803) with respect to the axial dimension of the lateral surface (804) at a given first cross-sectional level (e.g., through a proximal, central, or distal section of the stem (800)) defined by an axis transverse to the longitudinal axis of the stem (800) comprises a first ratio or fraction. The axial dimension of the medial surface (803) with respect to the axial dimension of the lateral surface (804) at a given second cross-sectional level (e.g., through a proximal, central, or distal section of the stem) defined by an axis transverse to the longitudinal axis of the stem (800) comprises a second ratio or fraction. The first ratio or fraction can be, for example, at least about 10%, 20%, 30%, 40%, 50%, 60%, 70%, 80%, 90%, 100%, 125%, 150%, 200%, 300%, or more of the second ratio or fraction. This results in an implant construct which has a large load bearing surface area on the medial surface (803) in the proximal region of the stem implant and a large load bearing surface area on the lateral surface of the distal region of the implant (802). Further, this construct produces an implant where the lateral surface dimension (e.g., width) of the proximal region (809) is relatively small when compared to that of the corresponding medial surface width (803), and the medial surface dimension of the distal region (810) is substantially smaller than that of the corresponding lateral surface dimension (802).

As a consequence of these medial to lateral surface area transitions, the implant may potentially be inserted into the native bone without the need for drilling or reaming prior to insertion. In addition, this construct effectively self-centers the implant within the intramedullary canal of the native bone, substantially reducing the risk of varus or valgus mal-positioning.

The embodiment illustrated in FIGS. 8 and 9 has a length in the range of, for example, about 100 mm to about 130 mm.

FIGS. 10a through 10i illustrates the continuously changing cross sectional area (900) and the differences in dimension, e.g., width of the medial (902) and lateral surfaces (901) of the femoral implant (905), the illustrated cross sections being shown at even increments of approximately 10 mm measured from the proximal end (FIG. 10a) to the distal end (FIG. 10i) respectively. In some embodiments as schematically illustrated, the ratio of medial (902) surface dimension to lateral (901) surface dimension at a particular transverse cross-section of the stem changes from a first, e.g., proximal or distal portion (e.g., FIG. 10a) of the stem to a second, e.g., proximal or distal portion (e.g., FIG. 10i) of the stem. In some embodiments, the ratio of medial (902) surface dimension to lateral (901) surface dimension (e.g., FIG. 10a) is greater than 1:1, such as greater than 1.1:1, 1.2:1, 1.3:1, 1.4:1, 1.5:1, 1.75:1, 2:1, 2.5:1, 3:1, 4:1, 5:1, 6:1, 7:1, 8:1, 9:1, 10:1, or more, while the ratio of medial (902) surface dimension to lateral (901) surface dimension (e.g., FIG. 10i) is less than 1:1, such as less than 0.9:1, 0.8:1, 0.7:1, 0.6:1, 0.5:1, 0.4:1, 0.3:1, 0.2:1 or less. In some embodiments, the ratio of medial (902) surface dimension to lateral (901) surface dimension changes (e.g., increases or decreases) by at least about 5%, 10%, 15%, 20%, 25%, 30%, 35%, 40%, 45%, 50%, 60%, 70%, 75%, 80%, 90%, 100%, 150%, 200%, 250%, 300%, 350%, 400%, 450%, 500%, 600%, 700%, 800%, 900%, 1000%, or more, or increases by at least 2×, 3×, 4×, 5×, 6×, 7×, 8×, 9×, 10×, 12×, 14×, 16×, 18×, 20×, 25×, or more with respect to two different transverse cross sections spaced longitudinally 10 mm, 20 mm, 30 mm, 40 mm, 50 mm, 60 mm, 70 mm, 80 mm, 90 mm, 100 mm, or more apart from each other, or spaced longitudinally by 10%, 20%, 30%, 40%, 50%, 60%, 70%, 80%, 90%, or more of the entire axial length of the implant, or transverse cross sections taken at the two ends of the implant. In some embodiments, the medial (902) surface dimension is greater than the lateral (901) surface dimension at the proximal end of the implant while the medial (902) surface dimension is smaller than the lateral (901) surface dimension at the distal end of the implant, or vice versa. However, in some embodiments the absolute medial (902) surface dimension is larger (or smaller) than the lateral (901) surface dimension at cross-sections throughout the axial length of the stem, while the ratio of medial (902) surface dimension to lateral (901) surface dimension changes with respect to at least two, three, or more different transverse cross sections.

Figure 11:
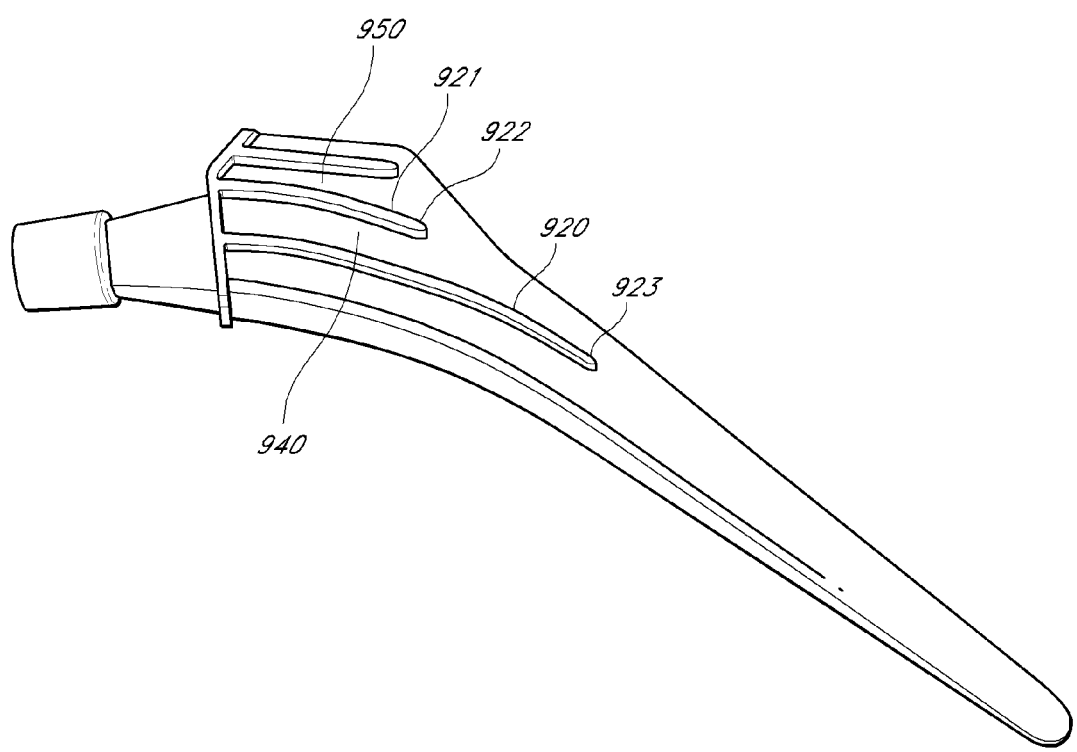
FIG. 11 is an anterior view of a femoral implant showing guide rails along the anterior surface of the implant.
Figure 12:
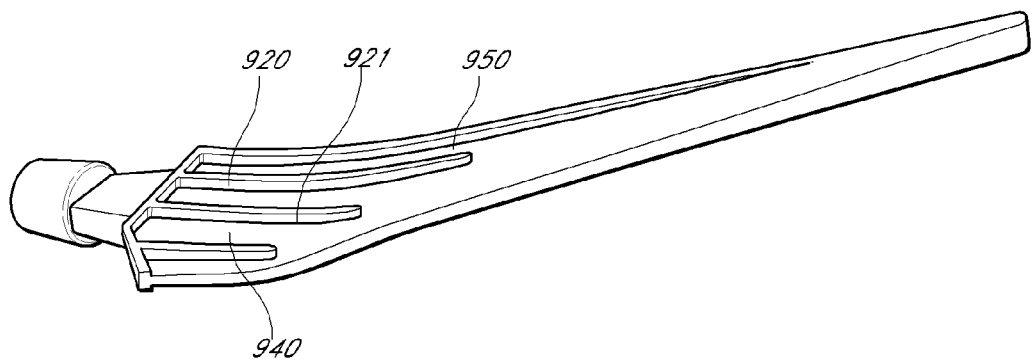
FIG. 12 is an anterolateral view of a femoral implant showing guide rails along the anterior surface.

FIG. 11 and FIG. 12 are an alternate embodiment of the femoral implant previously described, having one, two, three, four, or more supplemental generally axially-oriented guide rails (920) (921) located on the anterior and posterior surfaces of the implant, these guide rails (920) (921) disposed to provide supplemental centering and trajectory control of the implant during the final insertion within the proximal bone of the femur. The supplemental guide rails shown are positive protrusions located on the anterior and posterior surfaces of the proximal region of the implant, the medial rail (920) extending further distally than the lateral guide rail (921) such that the distal ends of the guide rails (922 and 923) engage cancellous bone sequentially as the implant is inserted into the native bone so as to assist in continuous guidance of the implant during the insertion of the implant. During the final insertion of the implant within the bone, cancellous bone tissue is compacted in the spaces between each of the guide rails (940 and 950) so as to increase the stability of the implant in the inserted position.

Figure 13:
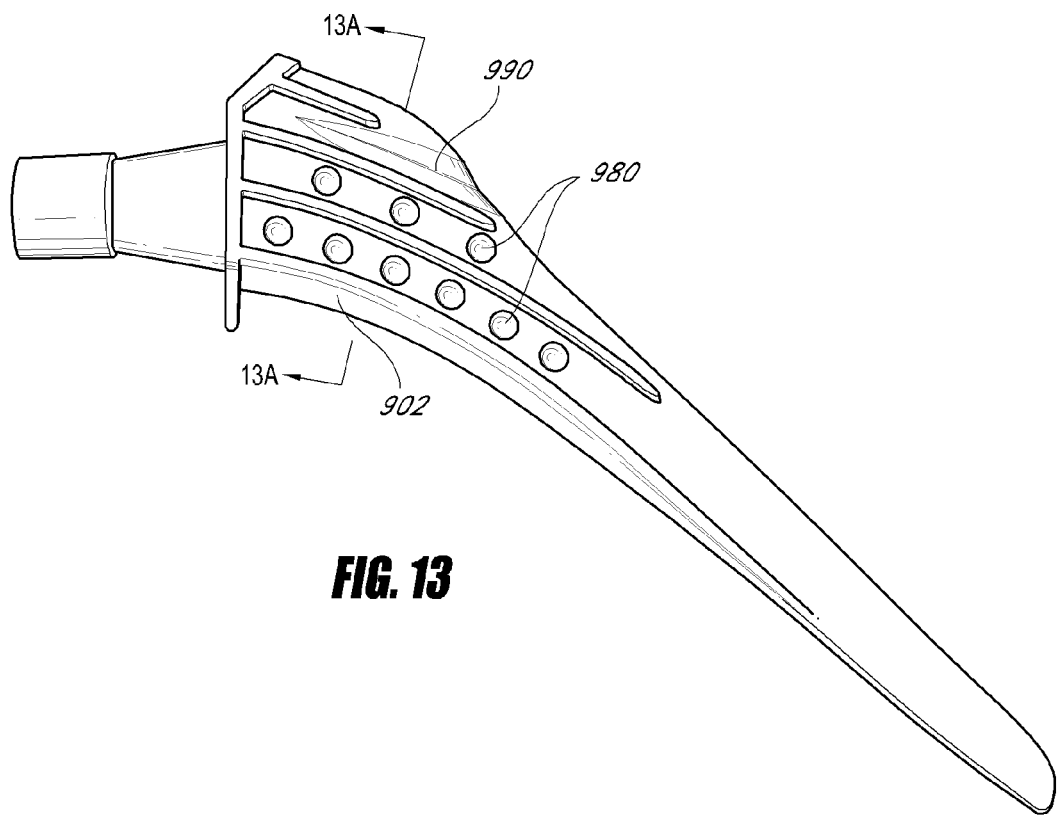
FIG. 13 is an anterior view of a femoral implant showing voids disposed in the proximal portion of the implant and a secondary keel feature in the lateral proximal portion of the implant.
Figure 13A:
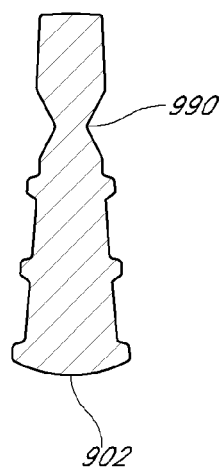
FIG. 13A is a cross-sectional view of the proximal section of the implant of FIG. 13 showing the secondary keel feature.
Figure 14:
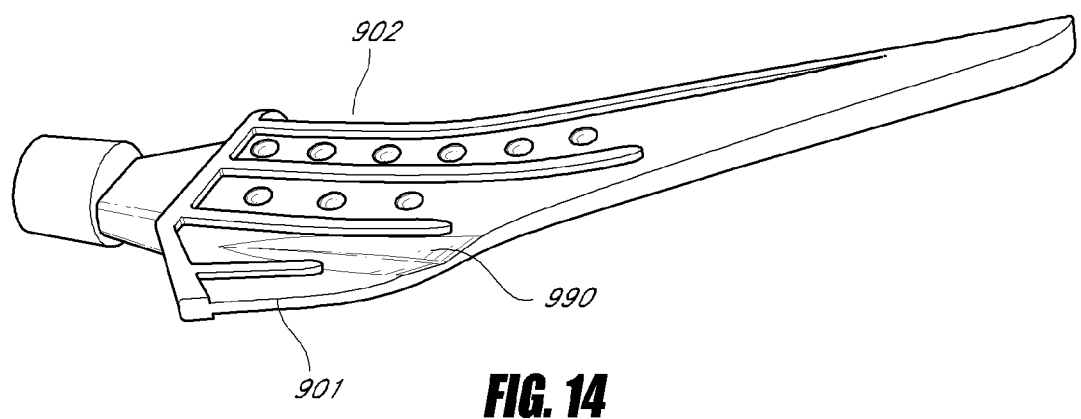
FIG. 14 is another view of the femoral implant of FIG. 13 showing the voids in the proximal portion and the lateral keel.

Referring now to FIG. 13 and FIG. 14, yet another embodiment of the femoral implant is described. The anterior and posterior surfaces of the proximal region of the implant have therein one, two, three, four, or more voids (980) disposed to accommodate compressed cancellous bone displaced during the insertion of the implant or to accommodate bone cement dispensed to assist fixation of the implant within the bone. Further illustrated is a secondary keel feature (990), disposed to substantially reduce the cross section of the lateral aspect of the implant locally in the proximal region so as to minimize the displacement of cancellous bone, thereby reducing insertion forces, and to minimize the tendency to introduce a medial turning moment during the final insertion. FIG. 13a is a cross section through the proximal region of the implant showing the reduced cross sectional dimension at the secondary keel (990) relative to, for example, the dimension of the medial surface (902) of the implant, the dimension at the secondary keel (990) being at least about 10%, 20%, 30%, 40%, 50%, 60%, 70%, or less with respect to the dimension of the medial surface (902).

Figure 15:
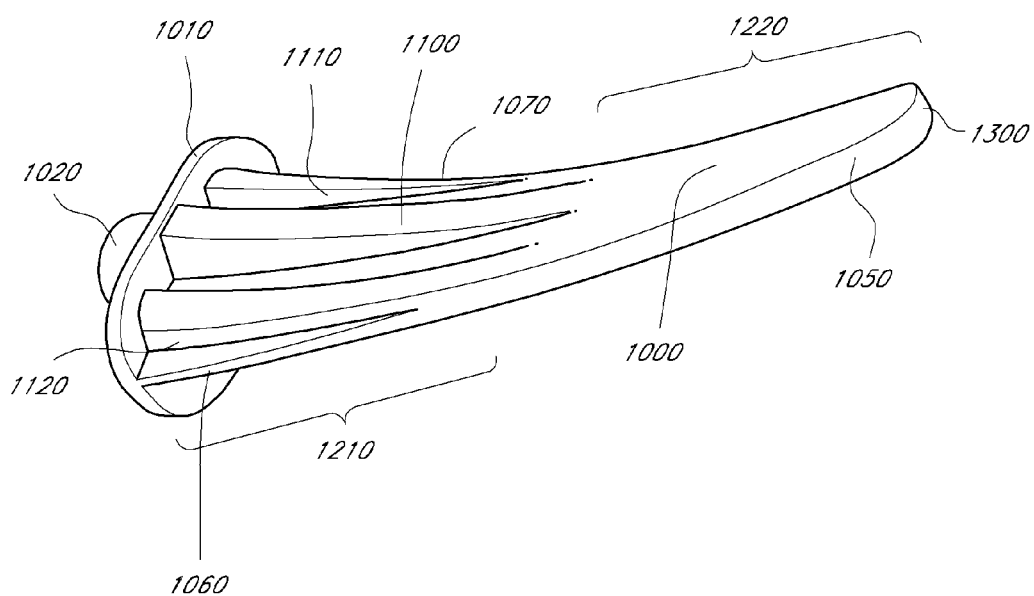
FIG. 15 is an anterolateral view of a humeral implant also showing stabilizing fins and arcuate medial and lateral surfaces.
Figure 16:
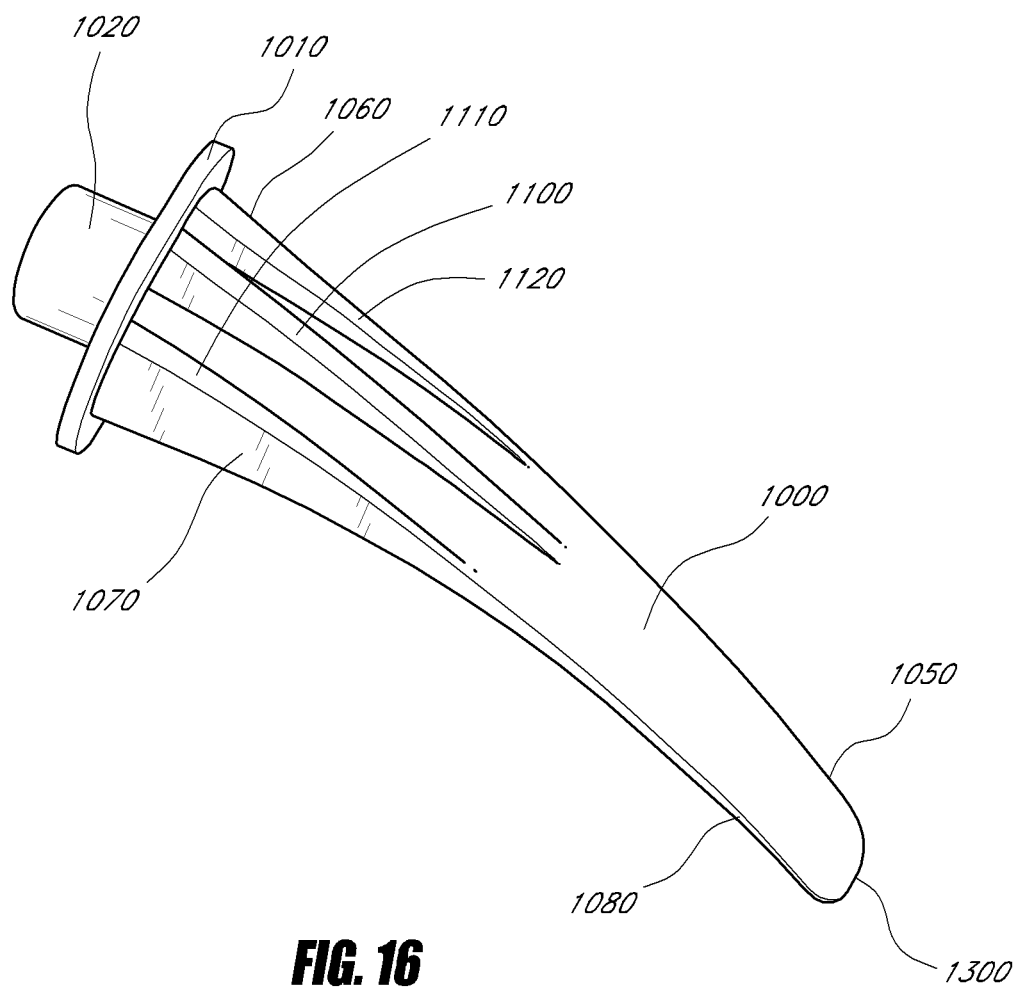
FIG. 16 is an anteromedial view of a humeral implant showing stabilizing fins and arcuate medial and lateral surfaces.
Figure 17:
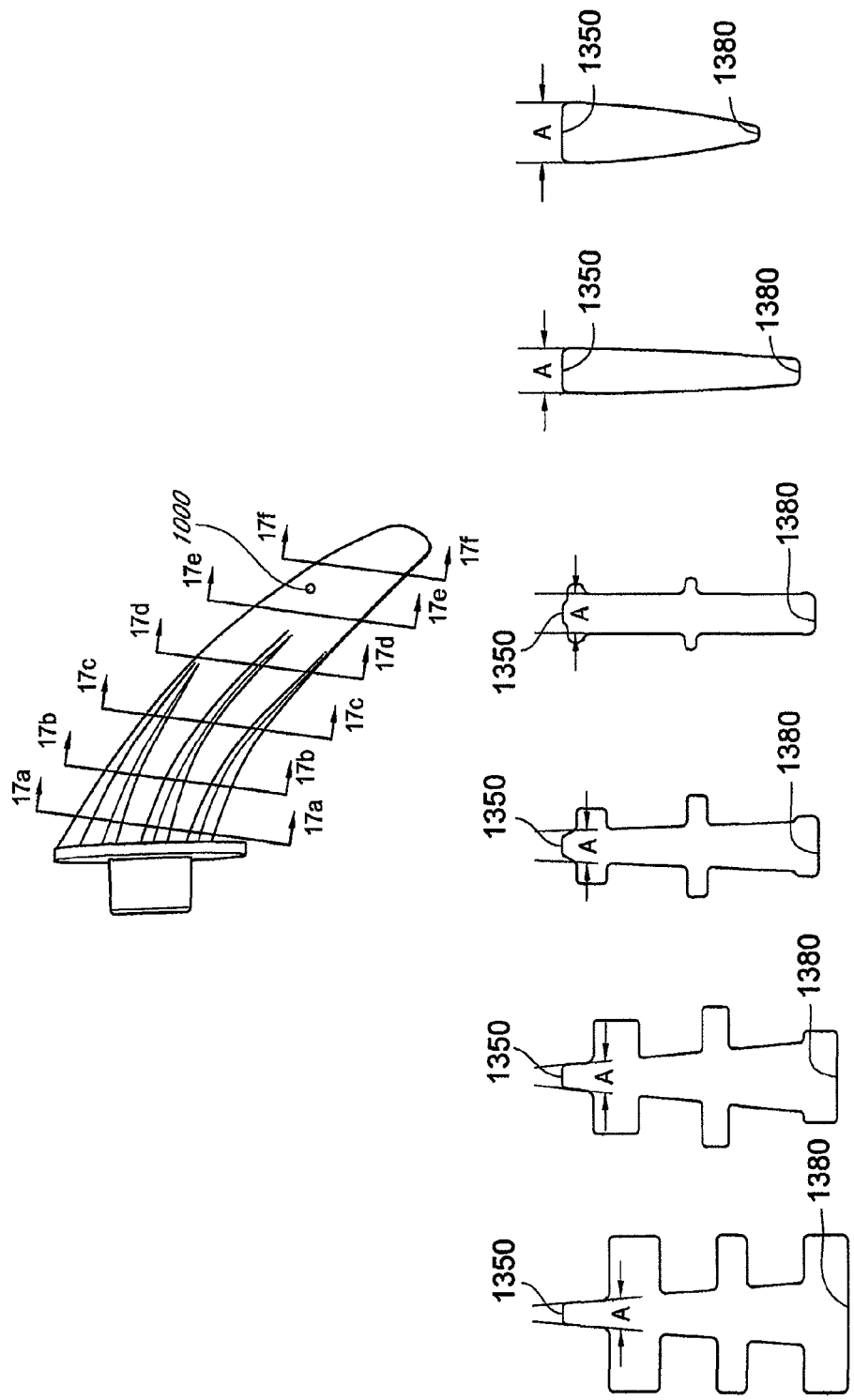
FIGS. 17A-17F are schematic cross sectional areas (not necessarily to scale) of a humeral implant from a first, e.g., proximal end to a second, e.g., distal end of the implant at approximately 10 mm intervals.

Referring now specifically to FIG. 15 and FIG. 16, another embodiment of a stem for use in humeral applications in shoulder joint arthroplasty is described. The implant (1000) is similar in construction principle to that previously described for the femoral stem, the stem having a proximal region (1210), a distal region (1220), a receiving means (e.g., a cavity, threaded region, complementary interlocking connector, joint, and the like) (1020) to accept an articulating element of a joint arthroplasty system, one, two, or more proximal flanges (1010) disposed to prevent subsidence of the implant stem into the cancellous bone after implantation, and one or a series of stabilization ribs (1120, 1100, and 1110) disposed to provide mechanical structure, resist rotation of the implant within the bone, and enhance the stability of the implant within the bone after implantation. The implant shown herein has an overall length of 70 mm to 90 mm.

The medial to lateral surface dimension relationship of the humeral implant can be similar to that previously described in detail for the femoral implant; the axial dimension (e.g., width) of the medial surface (1070) in the proximal region (1210) is substantially wider than the dimension, (e.g., width) of the corresponding lateral surface (1060) such that the axial dimension of the medial surface (1070) in the proximal region (1210) is at least about 5%, 10%, 15%, 20%, 25%, 30%, 35%, 40%, 50%, 75%, 100%, 200%, 300%, 400%, 500%, 600%, 700%, or more greater than the axial dimension of the corresponding lateral surface (1060) on an axis transverse to the longitudinal axis of the stem that includes the medial surface (1070). The width of the lateral surface (1050) in the distal region is substantially wider than that of the corresponding medial surface (1080), such that the axial dimension of the lateral surface (1050) in the distal region is at least about 5%, 10%, 15%, 20%, 25%, 30%, 35%, 40%, 50%, 75%, 100%, 200%, 300%, 400%, 500%, 600%, 700%, or more greater than the axial dimension of the corresponding medial surface (1080) on an axis transverse to the longitudinal axis of the stem that includes the lateral surface (1050). In some embodiments, the ratio of medial (902) surface dimension to lateral (901) surface dimension changes (e.g., increases or decreases) by at least about 5%, 10%, 15%, 20%, 25%, 30%, 35%, 40%, 45%, 50%, 60%, 70%, 75%, 80%, 90%, 100%, 150%, 200%, 250%, 300%, 350%, 400%, 450%, 500%, 600%, 700%, 800%, 900%, 1000%, or more, or increases by at least 2×, 3×, 4×, 5×, 6×, 7×, 8×, 9×, 10×, 12×, 14×, 16×, 18×, 20×, 25×, or more with respect to two different transverse cross sections spaced longitudinally 10 mm, 20 mm, 30 mm, 40 mm, 50 mm, 60 mm, 70 mm, 80 mm, 90 mm, 100 mm, or more apart from each other, or spaced longitudinally by 10%, 20%, 30%, 40%, 50%, 60%, 70%, 80%, 90%, or more of the entire axial length of the implant, or transverse cross sections taken at the two ends of the implant. FIGS. 17a to 17f illustrate the relative dimensions, e.g., widths of the lateral surface 1350 and the medial surface 1380, the figures represent transverse cross sections across the implant device progressing at 10 mm increments from the proximal end of the implant device (1000) to the distal end of the device. Further illustrated is the change in the origin of the included angle (A) between the anterior and posterior surfaces of the implant device from lateral to medial, or vice versa as shown by the transition of the base of a triangle formed by the included angle from the medial surface 1380 of the implant device in FIG. 17a to the lateral surface 1350 of the implant device in FIG. 17f. As illustrated, the angle A could change from positive to negative or negative to positive in successive cross-sections in a first direction to a second direction, and be, for example, less than about 80, 70, 60, 50, 40, 30, 20, 10, or less degrees in a first, e.g., proximal region of the implant and greater than about 20, 30, 40, 50, 60, 70, 80, or more degrees in a second, e.g., distal region of the implant. The below table lists one example of transverse dimensions at various cross-sectional levels as illustrated in FIGS. 17a-17f:

| Figure | Lateral Surface Dimension (mm) | Medial Surface Dimension (mm) | Medial:Lateral Surface Dimension Ratio |
|---|---|---|---|
| 17a | 1.0 | 6.0 | 6:1 |
| 17b | 2.0 | 5.0 | 5:2 |
| 17c | 3.0 | 4.5 | 3:2 |
| 17d | 3.5 | 3.5 | 1:1 |
| 17e | 4.5 | 2.5 | 5:9 |
| 17f | 7.0 | 2.5 | 5:14 |

Further shown in FIG. 15 and FIG. 16 are one or a series of stabilizing fins (1100, 1110, 1120) protruding from the anterior and/or posterior surfaces of the implant device. During the insertion of the proximal aspect of the implant (1210) said fins engage the soft cancellous bone tissue and compress it within the interspaces between the stabilizing fins thereby enhancing the stability within the bone, reducing the propensity to subside post operatively and improving the rotational stability of the implant within the native bone.

Figure 18:
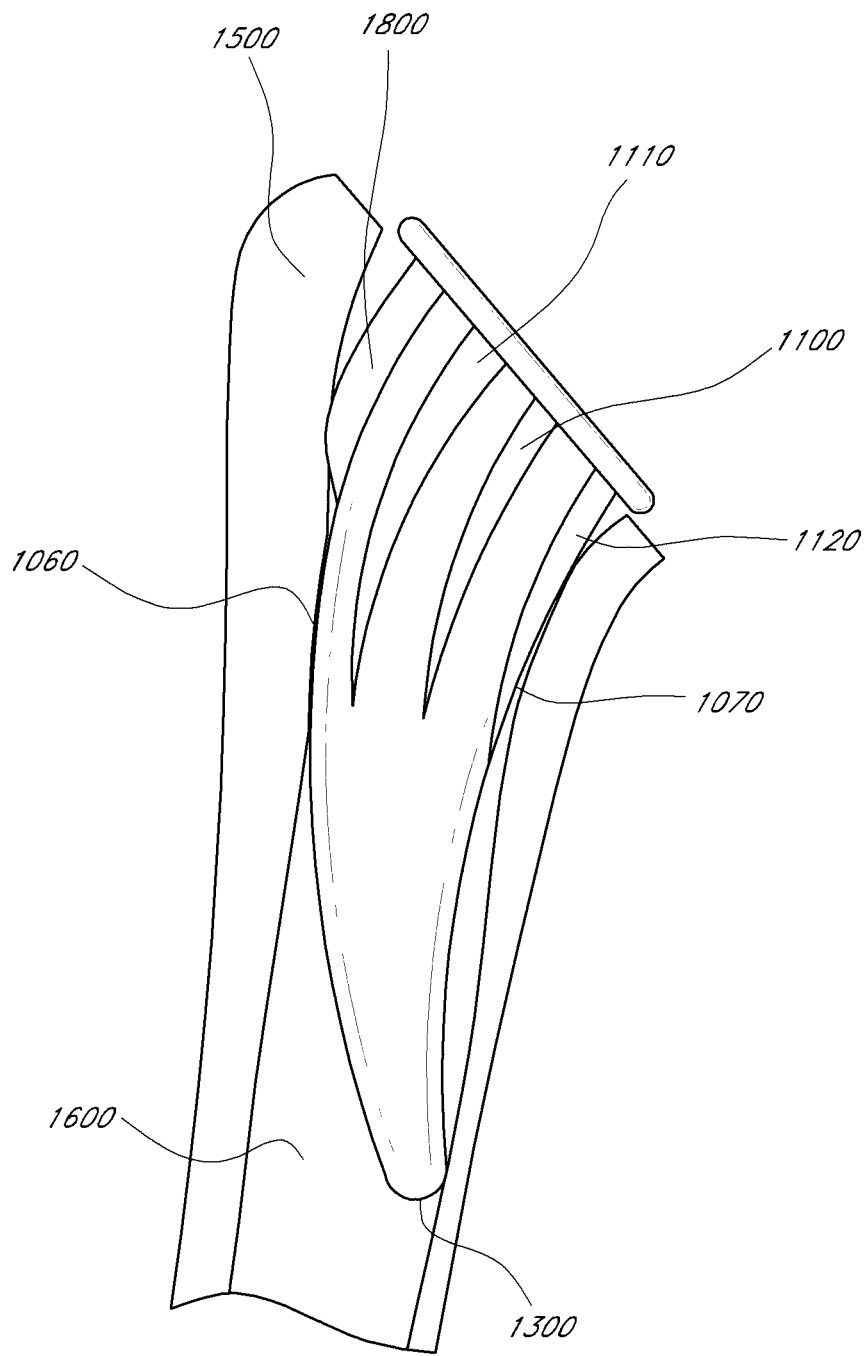
FIG. 18 is an image of a humeral implant placed within the bone.

Of further note is the arcuate nature of the medial and lateral surfaces (1070 and 1060 respectively). Referring now to FIG. 18, a radiographic image of one embodiment located within a humeral bone (1500) described in FIGS. 15, 16 and 17 (a-f) inclusive can be seen. The arcuate medial (1070) and lateral (1060) surfaces are shown engaging the intramedullary channel (1600). The larger medial surface (1070) is shown engaging the intramedullary channel (1600). The larger medial surface (1070) is shown engaging the cortical bone at the medial aspect of the humerus in the proximal region while the wider lateral surface (1060) is shown engaging the cortical bone distally.

Figure 19:
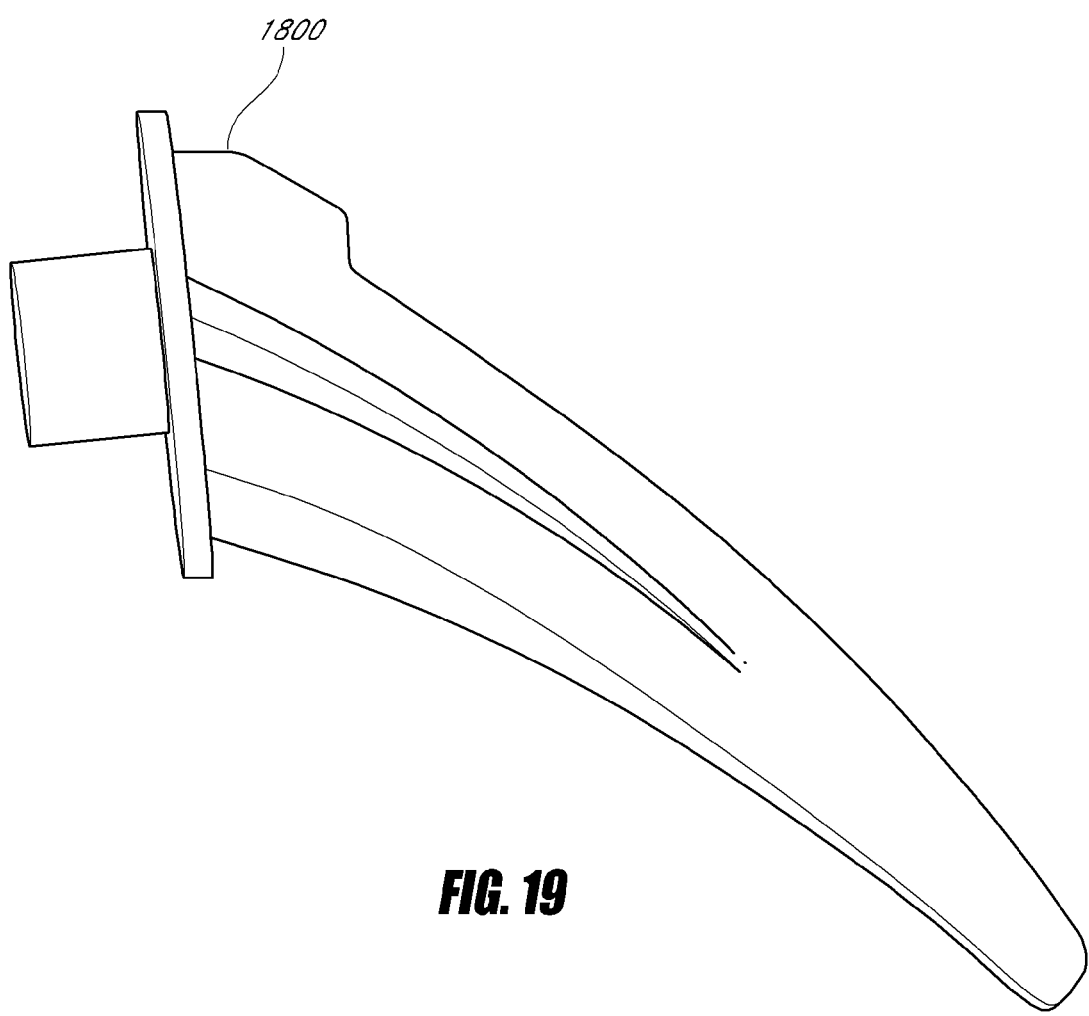
FIG. 19 is an anteromedial view of a humeral implant showing a supplemental stabilization fin.
Figure 20:
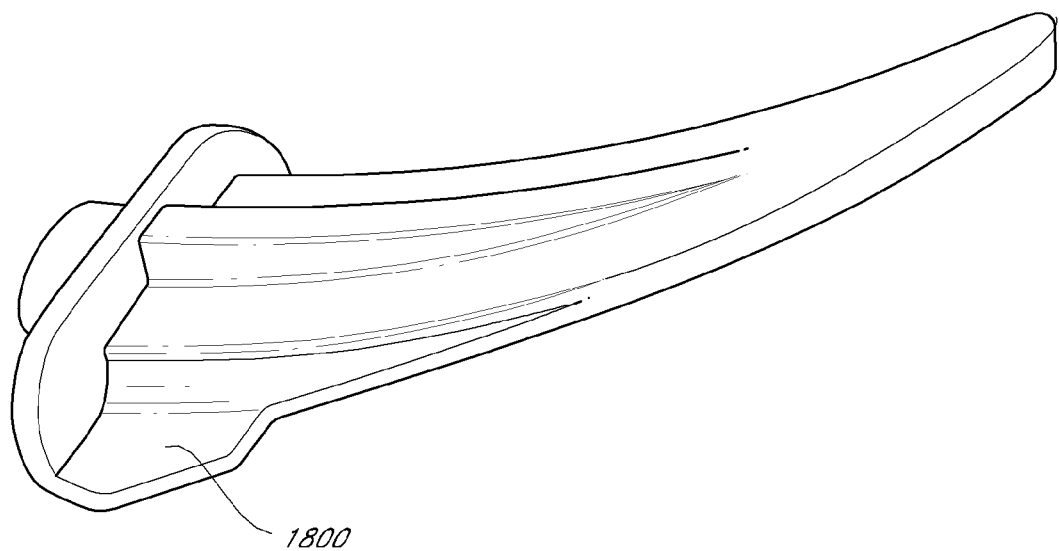
FIG. 20 is an anterolateral view of a humeral implant showing a supplemental stabilization fin.

Referring now to FIGS. 19 and 20, an alternate embodiment of the humeral implant device previously described is shown. The humeral implant has a supplemental stabilization fin (1800) located, for example, at the lateral aspect of the proximal surface. Fin (1800) is disposed to further enhance the mechanical stability of the final implant within the bone and resist torsional loads on the implant to bone interface.

Figure 21:
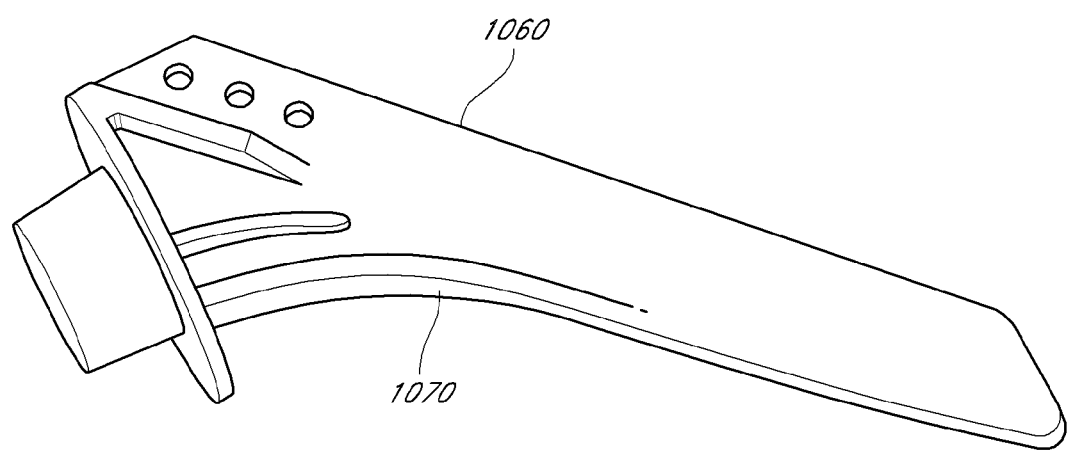
FIG. 21 is an anterior view of a humeral implant showing an arcuate medial surface and straight lateral surface.
Figure 22:
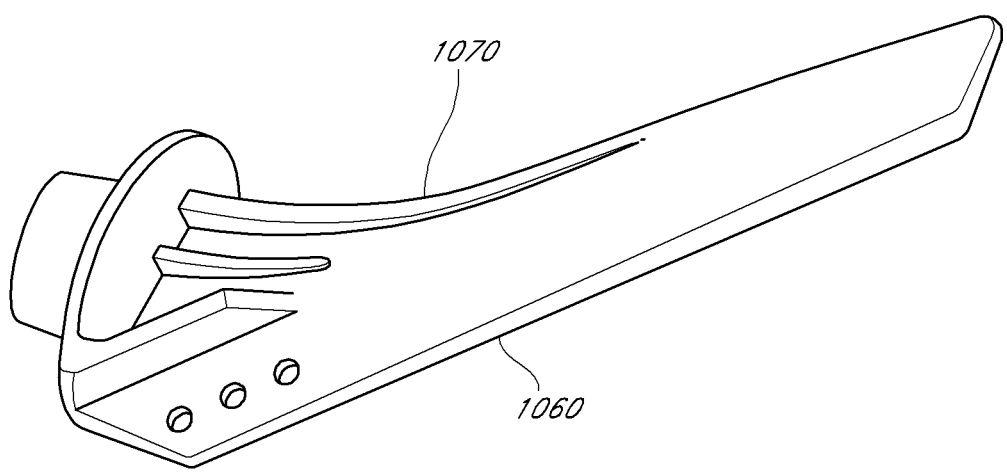
FIG. 22 is another view of a humeral implant showing an arcuate medial surface and straight lateral surface.

FIGS. 21 and 22 are alternate embodiments of a humeral stem having an curved, e.g., arcuate medial surface (1070) and a straight lateral surface (1060).

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. Certain embodiments of humeral implants as described, for example, in U.S. patent application Ser. No. 13/088,976 to Gunther filed on Apr. 18, 2011 and glenoid implants described, for example, in U.S. Pat. Pub. No. 2010/0249938 to Gunther et al., both of which are hereby incorporated by reference in their entireties, can be used or modified for use with stem embodiments as described herein In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. For example, while the features and embodiments shown herein have been described in the context of applications specific to individual bone structures, the various features described can be used individually, or in combination, to produce prosthetic bone implants for use in multiple and varied skeletal applications. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:

1. An implant for use in a long bone during joint arthroplasty, said implant comprising:
a first end;
a second end comprising a blunt tip; and
a stem of the implant comprising a proximal portion and a distal portion, wherein the proximal portion and the distal portion are configured to be inserted within the medullary canal of the long bone and disposed between the first and second ends, wherein
the proximal portion of the stem comprises an anterior surface, a posterior surface, a medial surface and a lateral surface, wherein a dimension of said medial surface taken in a first plane substantially perpendicular to the longitudinal axis of the implant and at a level in the vicinity of a proximal end of the stem is greater than a dimension of said lateral surface taken in the same first plane, and
the distal portion of the stem comprises an anterior surface, a posterior surface, a medial surface, and a lateral surface, wherein a dimension of said lateral surface taken in a second plane substantially perpendicular to the longitudinal axis of the implant and at a level in the vicinity of a distal end of the stem, the second plane spaced distally apart from the first plane is greater than a dimension of the medial surface taken in the same second plane,
wherein the second plane is spaced at least 50% longitudinally distally apart from the first plane with respect to the entire axial length of the implant.

2. The implant of claim 1, wherein the medial surface dimension taken in the first plane is at least 5% greater than the lateral surface dimension in the first plane and the lateral surface dimension taken in the second plane is at least 5% greater than the medial surface dimension taken in the same second plane.

3. The implant of claim 1, wherein said implant is a femoral implant.

4. The implant of claim 3, where the proximal portion of the stem further comprises a keel arising from the lateral surface, a medial origin of the keel comprising a section narrower in an anterior to posterior measurement than adjacent sections of the stem medially and the keel laterally to said medial origin section.

5. The implant of claim 3, where said implant further comprises at least one axially oriented longitudinal protrusion on the anterior and posterior surfaces of the proximal portion of the stem.

6. The implant of claim 5, where said stem further comprises at least two protrusions, one relatively medial and one relatively lateral on the anterior and posterior surfaces of the proximal portion of the stem.

7. The implant of claim 6, wherein the medial protrusion extends further distally on the stem than the lateral protrusion extends distally.

8. The implant of claim 1, where said implant is a humeral implant.

9. The implant of claim 8, where said implant further comprises a proximal collar disposed between the first end and the stem of the implant.

10. The implant of claim 8, further comprising at least one anterior or posterior protrusion disposed along the proximal portion of the stem.

11. The implant of claim 8, where the stem further comprises a curved medial surface and a curved lateral surface along the length of the stem.

12. The implant of claim 8, where the stem further comprises a curved medial surface and a substantially straight lateral surface along the length of the stem.

13. The implant of claim 1, wherein the second plane is spaced at least 60% longitudinally distally apart from the first plane with respect to the entire axial length of the implant.

14. The implant of claim 1, wherein the second plane is spaced at least 30mm longitudinally distally apart from the first plane with respect to the entire axial length of the implant.

15. The implant of claim 1, wherein the second plane is spaced at least 50mm longitudinally distally apart from the first plane with respect to the entire axial length of the implant.

16. An implant for use in a long bone during joint arthroplasty, said implant comprising:
   a first end;
   a second end comprising a blunt tip; and
   a stem of the implant comprising a proximal portion and a distal portion, wherein the proximal portion and the distal portion are configured to be inserted within the medullary canal of the long bone and disposed between the first and second ends, wherein
   the proximal portion of the stem comprises an anterior surface, a posterior surface, a medial surface and a lateral surface, wherein a dimension of said medial surface taken in a first plane substantially perpendicular to a longitudinal axis of the implant and at a level in the vicinity of a proximal end of the stem is greater than a dimension of said lateral surface taken in the same first plane, and
   the distal portion of the stem comprises an anterior surface, a posterior surface, a medial surface, and a lateral surface, wherein a dimension of said lateral surface taken in a second plane substantially perpendicular to the longitudinal axis of the implant and at a level in the vicinity of a distal end of the stem, the second plane spaced distally apart from the first plane is greater than a dimension of the medial surface taken in the same second plane,
   wherein the second plane is spaced at least 30mm longitudinally distally apart from the first plane.

17. The implant of claim 16, wherein the second plane is spaced at least 50mm longitudinally distally apart from the first plane.

18. The implant of claim 16, wherein the medial surface dimension taken in the first plane is at least 5% greater than the lateral surface dimension in the first plane and the lateral surface dimension taken in the second plane is at least 5% greater than the medial surface dimension taken in the same second plane.

19. The implant of claim 16, wherein said implant is a femoral implant.

20. The implant of claim 19, where the proximal portion of the stem further comprises a keel arising from the lateral surface, a medial origin of the keel comprising a section narrower in an anterior to posterior measurement than adjacent sections of the stem medially and the keel laterally to said medial origin section.

21. The implant of claim 19, where said implant further comprises at least one axially oriented longitudinal protrusion on the anterior and posterior surfaces of the proximal portion of the stem.

22. The implant of claim 21, where said stem further comprises at least two protrusions, one relatively medial and one relatively lateral on the anterior and posterior surfaces of the proximal portion of the stem.

23. The implant of claim 22, wherein the medial protrusion extends further distally on the stem than the lateral protrusion extends distally.

24. The implant of claim 16, where said implant is a humeral implant.

25. The implant of claim 24, where said implant further comprises a proximal collar disposed between the first end and the stem of the implant.

26. The implant of claim 24, further comprising at least one anterior or posterior protrusion disposed along the proximal portion of the stem.

27. The implant of claim 24, where the stem further comprises a curved medial surface and a curved lateral surface along the length of the stem.

28. The implant of claim 24, where the stem further comprises a curved medial surface and a substantially straight lateral surface along the length of the stem.

* * * * *